Oct. 6, 1959 H. L. GREENE Plant Pat. 1,871
ROSE PLANT
Filed Oct. 6, 1958
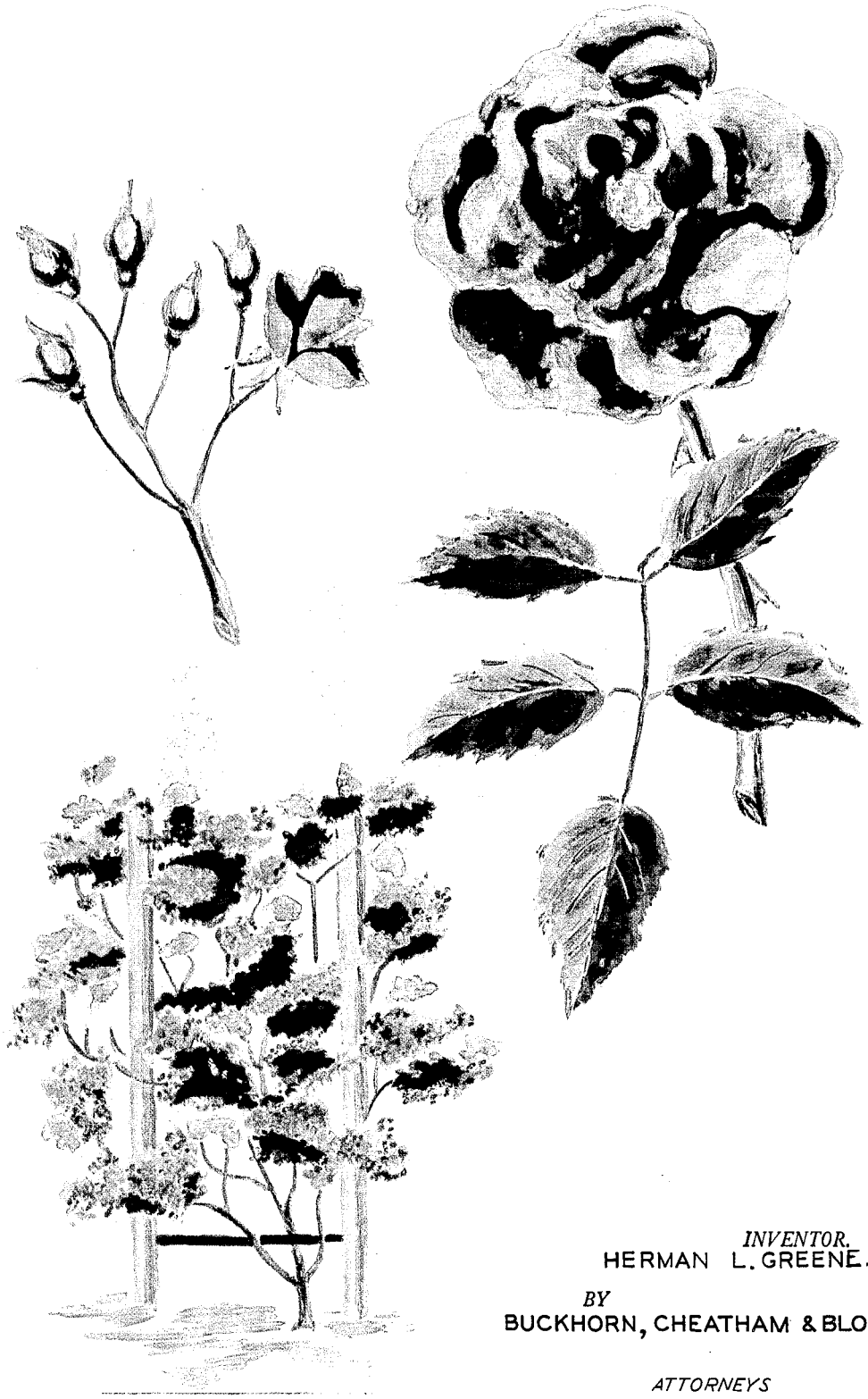
INVENTOR.
HERMAN L. GREENE.
BY
BUCKHORN, CHEATHAM & BLORE
ATTORNEYS United States Patent Office Plant Pat. 1,871
Patented Oct. 6, 1959

1,871

ROSE PLANT

Herman Louis Greene, Portland, Oreg.

Application October 6, 1958, Serial No. 765,687

1 Claim. (Cl. 47—61)

The present invention relates to a new and distinct variety of rose plant of the climbing floribunda class, which originated as a cultivated sport of the variety "Alain," unpatented.

This new sport was discovered by me in a cultivated row of "Alain" roses, which were being grown by me in my nursery located near Portland, Oregon. I noticed that one of the plants was different in nature from the other plants—the flowers were much lighter in color and much larger, and the plant itself exhibited a climbing habit. I immediately made plans to preserve, asexually reproduce and observe this sport to determine whether or not the characteristics of the flower and the climbing habit of the plant were permanent in nature, and also whether they were transmissible by asexual reproduction.

Subsequently, by my observations and also by asexual reproduction by budding by me at my nursery plantings near Portland, Oregon since 1953, I have established conclusively that all of the characteristics of the new plant are permanent in nature, and that the distinguishing characteristics are held through succeeding propagations by budding. At present about 1000 plants have been so produced.

The blooms of this new variety of rose are large, up to 3½ inches in diameter, are a bright, flame-red in color, have a very pronounced fragrance, are semi-double, and bloom in large clusters, which have as many as 20 blooms in one cluster. The blooms have long, sturdy stems, which make them desirable for cut flowers as well as for garden decoration. The foliage is a light green, and the leaves are large in size and shiny and satiny. The plants are very hardy, having been tested along with several other varieties of floribundas in a planting near Milwaukee, Wisconsin, and this new variety was the only one to survive a severe winter with no damage. It is also a very vigorous grower, having attained a height of from eight to ten feet the first year. Another distinguishing characteristic of this rose is that most all of the plants bloom the first year, which is not common to all climbing roses. This rose grows vigorously, and blooms continuously from April until November, one of the last roses blooming.

The accompanying illustration shows, in full color a specimen plant, a cluster in the bud, and a full bloom of actual size.

The following is a detailed description of my new variety:

Flower: Blooms profusely from April to November.
*Size.*—Up to 3½ inches in diameter.
*Borne.*—In large clusters on long, sturdy stems.
*Quantity of bloom.*—Abundant, outdoors.
*Fragrance.*—Strong.
*Shape.*—Globular at first, becoming open-cupped.
*Petalage.*—Semi-double. Average 24–27 petals.
*Texture.*—Velvety.
Plant: *Form.*—Climber.
*Height.*—From eight to ten feet, first year.
*Growth.*—Vigorous, hardy.
Branches: Many, which climb.
Foliage: *Quantity.*—Abundant.
*Size of leaf.*—Large.
*Texture.*—Shiny and satiny.
Blooming age: Almost all plants bloom in first year.

The following is a brief description of my new variety, with color terminology in accordance with Maerz and Paul Color Dictionary.

| Part | Plate | Letter | No. |
|---|---|---|---|
| Deepest shade of bloom | 2 | L | 5 |
| Palest shade of bloom | 2 | L | 1 to 2 |
| Top of leaf | 23 | L | 7 |
| Underside of leaf | 21 | L | 2 |
| Stem | 21 | L | 7 |

Having thus described my invention, I claim:

A new and distinct variety of climbing floribunda rose plant, substantially as shown and described, characterized particularly by its large, brilliant flame-red flowers; its climbing nature; its vigorous constitution; its continuous blooming habit; its vigorous growing habit; the fact that it usually blooms the first year; the large number of blooms in a cluster, and the fragrance of the flowers.

No references cited.